United States Patent
Yundt-Pacheco

(10) Patent No.: US 7,711,503 B2
(45) Date of Patent: *May 4, 2010

(54) SYSTEM AND METHOD FOR INTEGRATING THE INTERNAL AND EXTERNAL QUALITY CONTROL PROGRAMS OF A LABORATORY

(75) Inventor: John Yundt-Pacheco, Plano, TX (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/273,212

(22) Filed: Nov. 18, 2008

(65) Prior Publication Data

US 2009/0076755 A1    Mar. 19, 2009

Related U.S. Application Data

(63) Continuation of application No. 10/428,584, filed on May 2, 2003, now Pat. No. 7,467,054.

(51) Int. Cl.
*G01D 18/00* (2006.01)

(52) U.S. Cl. .......................... 702/84; 700/109

(58) Field of Classification Search .................. 702/84
See application file for complete search history.

(56) References Cited

U.S. PATENT DOCUMENTS 4,858,154 A * 8/1989 Anderson et al. ............ 702/81
6,445,969 B1 * 9/2002 Kenney et al. ............. 700/108
2001/0005821 A1 * 6/2001 Ottosson .................... 702/185

FOREIGN PATENT DOCUMENTS

| JP | 9502811    | 3/1997 |
|----|------------|--------|
| JP | 2001-76054 | 3/2001 |
| JP | 2003-29825 | 1/2003 |

* cited by examiner

*Primary Examiner*—Bryan Bui
*Assistant Examiner*—Jonathan Teixeira Moffat
(74) *Attorney, Agent, or Firm*—Stinson Morrison Hecker LLP

(57) ABSTRACT

A system and method that enables a laboratory to integrate its internal and external quality control programs to thereby control the quality of its laboratory testing services. The system has a storage device and a processor operable to maintain in the storage device a database identifying a plurality of laboratory tests and the corresponding internal laboratory statistical data, group statistical summary data and control rules. The processor is also operable to calculate a control range for a specified laboratory test by applying the group statistical summary data (and, in some cases, the internal laboratory statistical data) to the control rule corresponding to the specified laboratory test. Preferably, the processor is also operable to receive a test result from a laboratory instrument, and determine whether the test result falls within the calculated control range for the specified laboratory test. Various exemplary embodiments of the system and associated method are provided.

45 Claims, 7 Drawing Sheets

SYSTEM AND METHOD FOR INTEGRATING THE INTERNAL AND EXTERNAL QUALITY CONTROL PROGRAMS OF A LABORATORY

CROSS-REFERENCE TO RELATED APPLICATIONS

This application is a Continuation of U.S. patent application Ser. No. 10/428,584, filed on May 2, 2003, which is hereby incorporated herein by reference.

STATEMENT REGARDING FEDERALLY SPONSORED RESEARCH OR DEVELOPMENT

Not applicable.

FIELD OF THE INVENTION

The present invention relates generally to laboratory testing services and, more particularly, to a system and method that enables a laboratory to integrate its internal and external quality control programs to thereby control the quality of its laboratory testing services.

BACKGROUND OF THE INVENTION

There are many techniques used to test the functionality of laboratory instruments for the purpose of controlling the quality of laboratory testing services. One common practice is to test a stable specimen having predetermined characteristics (also known as a quality control specimen) and verify that the test result falls within a predicted range of acceptable values (also known as a control range) for a specified laboratory test. Typically, the control range is either derived from the manufacturer of the quality control material, arrived at by internal laboratory testing (i.e., by applying internal laboratory statistical data to a control rule), or a combination of the two. If the test result falls within the control range, the laboratory instrument is deemed to be functioning properly and is thus suitable for testing actual patient specimens. On the other hand, the laboratory instrument is deemed to be malfunctioning if the test result does not fall within the control range. This practice is referred to as the internal quality control program of the laboratory.

In addition to implementing an internal quality control program, many laboratories participate in external quality control programs (also known as peer-group quality control programs). A typical peer-group quality control program consists of a collection of participating laboratories that test quality control specimens from the same source and submit the test results to a central agency. The central agency then computes group statistical summaries of the submitted test results and sends reports back to the participating laboratories. In this manner, each participating laboratory is able to review reports that quantify the variation in test results experienced among participating laboratories.

In the past, the participating laboratories would record a month's worth of test results and mail the results to the central agency at the end of the month. This step would take approximately 35 days. The central agency would then compile the test results received from the participating laboratories, compute group statistical summaries of the test results, and mail reports back to the participating laboratories. This step would take approximately 15-25 days. The disadvantage to this practice was that the inherent time delay (approximately 50-60 total days) limited the usage of the reports to a retrospective look at the quality of the testing services provided by the participating laboratories. As a result, even if the reports indicated a malfunction of a particular laboratory instrument, hundreds or thousands of actual patient specimens may have already been tested by the instrument.

With the advent of the Internet and other communication networks, many peer-group quality control programs are now able to process test results dynamically on a real-time basis. In practice, a participating laboratory transmits test results to the central agency over the Internet on a regular basis. The central agency then receives the test results, updates the group statistical summaries to include the newly transmitted test results, and immediately transmits reports back to the participating laboratory over the Internet. The advantage to this practice is that the participating laboratory receives the reports in a much timelier fashion than the previous mail-in approach.

Traditionally, the internal quality control program of a laboratory has functioned independently of the external quality control program. The reports received from the central agency (whether in hard-copy form via mail or in electronic form via the Internet) are typically reviewed by someone in a managerial role within the laboratory for the purpose of identifying extreme variations between the data in the group statistical summaries and the internal laboratory statistical data used for internal laboratory testing. If only small variations are detected, nothing is done to the laboratory test system and the internal quality control program remains unchanged. However, if extreme variations are detected, it may provoke an inquiry as to the origin of the variations to thereby trigger a re-calibration of one or more laboratory instruments. Thus, the external quality control program is only utilized to correct large errors in the laboratory test system, while ignoring smaller and more tolerable errors.

BRIEF SUMMARY OF THE INVENTION

The present invention is directed to a system and method that enables a laboratory to integrate its internal and external quality control programs to thereby control the quality of its laboratory testing services.

The system of the invention comprises a storage device and a processor operable to maintain in the storage device a database identifying various sets of relational data. One set of relational data comprises a plurality of laboratory tests and the internal laboratory statistical data corresponding to each of the laboratory tests. Another set of relational data comprises the plurality of laboratory tests and the group statistical summary data corresponding to each of the laboratory tests. Yet another set of relational data comprises the plurality of laboratory tests and the control rules corresponding to each of the laboratory tests. The processor is also operable to calculate a control range for a specified laboratory test by applying the group statistical summary data (and, in some cases, the internal laboratory statistical data) to the control rule corresponding to the specified laboratory test. Preferably, the processor is also operable to receive a test result from a laboratory instrument, and determine whether the test result falls within the calculated control range for the specified laboratory test.

Similarly, the computerized method of the invention comprises maintaining a database identifying a plurality of laboratory tests and the corresponding internal laboratory statistical data, group statistical summary data and control rules. The method also comprises calculating a control range for a specified laboratory test by applying the group statistical summary data (and, in some cases, the internal laboratory statistical data) to the control rule corresponding to the specified laboratory test. Preferably, the method also comprises receiving a test result from a laboratory instrument, and determining whether the test result falls within the calculated control range for the specified laboratory test.

The present invention will be better understood from the following detailed description of the invention, read in connection with the drawings as hereinafter described.

DETAILED DESCRIPTION OF PREFERRED EMBODIMENT

The present invention is directed to a system and method that enables a laboratory to integrate its internal and external quality control programs to thereby control the quality of its laboratory testing services. The invention will be described hereinbelow with reference to various technical terms, including "processor," "storage device" and "database." It should be understood that as used herein (including in the claims), the term "processor" means either a single processor that performs the described processes or a plurality of processors that collectively perform the described processes; the term "storage device" means either a single storage device that stores the described database(s) or a plurality of storage devices that collectively store the described database(s); and the term "database" means either a single database that identifies the described sets of data or a plurality of databases that collectively identify the described sets of data. Thus, the system and method may be implemented with any number of processor(s), storage device(s) and database(s) without departing from the scope of the invention.

Figure 1:
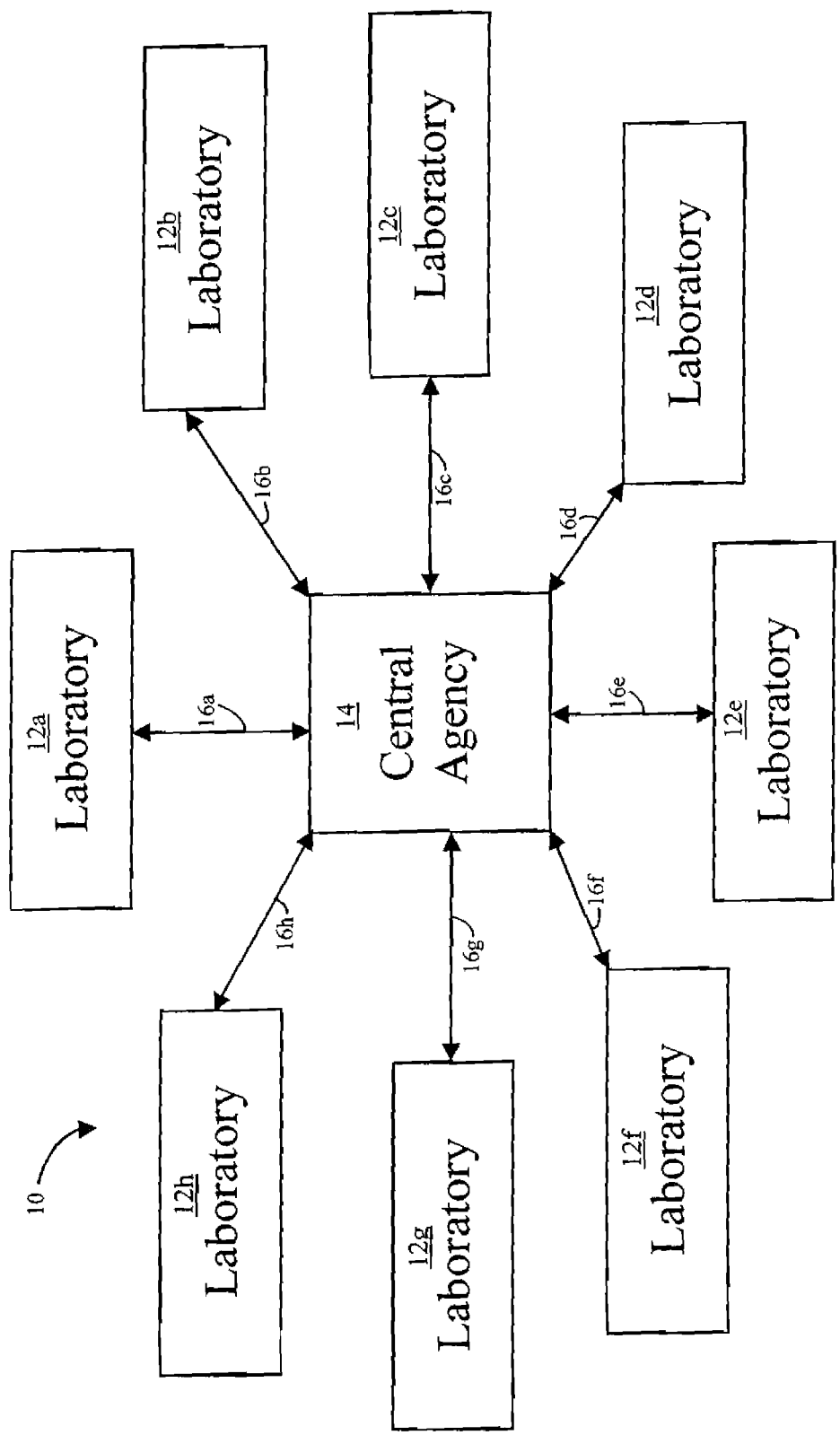
FIG. 1 is a block diagram of a system for integrating the internal and external quality control programs of a laboratory, in accordance with the present invention.

Referring to FIG. 1, a system in accordance with the present invention is designated generally as reference numeral 10. System 10 includes a plurality of participating laboratories 12a-12h in communication with a central agency 14 over a plurality of communication links 16a-16h. Although eight laboratories have been shown in FIG. 1 (as would be customary for applications involving hospital and reference laboratories), it should be understood that system 10 may include hundreds or even thousands of laboratories. As will be described in greater detail hereinbelow, each of laboratories 12a-12h is able to integrate its internal and external quality control programs by utilizing the group statistical summary data generated by central agency 14 in connection with the computation of control ranges for its internal laboratory testing.

Communication links 16a-16h may comprise any type of communication network that is capable of transporting data between laboratories 12a-12h and central agency 14, such as the Internet. Of course, other types of communication networks could also be used, such as any type and/or combination of local area networks, wide area networks, X.25, and ATM. Alternatively, communication links 16a-16h may comprise any type of dedicated line between laboratories 12a-12h and central agency 14.

As will now be described with reference to FIGS. 2, 3 and 4, participating laboratories 12a-12h may have the same system configuration, different system configurations, or a combination of the two (i.e., some laboratories may have the same system configuration and others may have different system configurations). To show the various ways in which laboratories 12a-12h could be implemented, three exemplary embodiments of system configurations for laboratories 12a-12h will be described hereinbelow with reference to laboratories 12a, 12b and 12c. One skilled in the art will understand, however, that other system configurations could also be implemented in accordance with the present invention.

Figure 2:
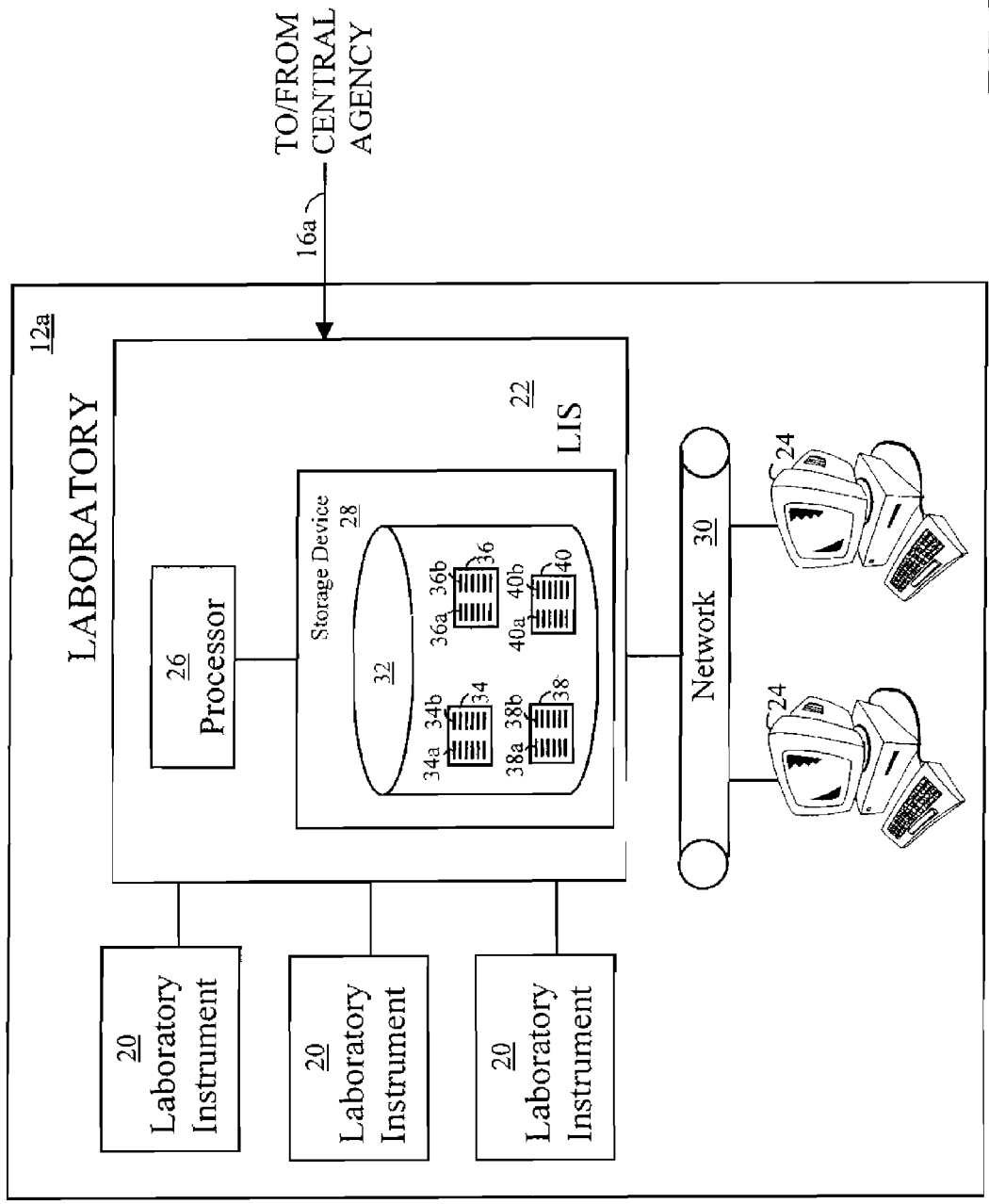
FIG. 2 is a block diagram of a first exemplary embodiment of one of the laboratories of FIG. 1.

Referring now to FIG. 2, a first exemplary embodiment of a system configuration for participating laboratories 12a-12h is shown with reference to laboratory 12a. Laboratory 12a includes one or more laboratory instruments 20 connected to a laboratory information system (LIS) 22, which is in turn connected to one or more workstations 24 used by laboratory workers. While laboratory instruments 20, LIS 22 and workstations 24 are shown as being co-located together within the same laboratory, it should be understood that one or more of these system elements could be located at a remote location (with suitable connections to the other system elements).

As is known in the art, laboratory instruments 20 may be utilized to perform a variety of different laboratory tests on quality control specimens prior to testing actual patient specimens. Laboratory instruments 20 may include identical instruments from the same manufacturer, different instruments from the same manufacturer, or different instruments from a variety of manufacturers. Examples of such laboratory instruments include the Olympus AU2700, the Abbott CELL-DYN 1700, the Vitros 950, the DPC Immulite 2000, the Bayer Rapidpoint 400, and the Dade Behring PFA 100. Of course, other types of laboratory instruments could also be used. Although three laboratory instruments 20 have been shown in FIG. 2 for ease of illustration, it should be understood that laboratory 12a may include any number of laboratory instruments that are required for the provision of laboratory testing services. Typically, each of laboratory instruments 20 is connected to LIS 22 via an RS-232 serial connection, although other types of connections could also be used.

LIS 22 comprises a computing system that includes a processor 26 and a storage device 28. Examples of well-known computing systems that are suitable for use with the present invention include server computers, multiprocessor computers and mainframe computers, although other computing systems could also be used. Processor 26 is operable to execute computer-readable instructions stored on a computer-readable medium to thereby perform the various processes of the present invention, as will be described in greater detail hereinbelow. The computer-readable instructions may be coded using the Delphi programming language, although other programming languages could also be used, such as C, C++, Visual Basic, Java, Smalltalk, Eiffle, PERL and FORTRAN. The computer-readable medium may include any type of computer memory, such as floppy disks, conventional hard disks, CD-ROMS, Flash ROMS, nonvolatile ROM and RAM.

Workstations 24 each comprise a computing system, such as a personal computer or a character terminal, which may be used by a laboratory worker to initiate certain processes of the invention (e.g., the performance of laboratory tests on laboratory instruments 20 and/or the synchronization of data between laboratory 12a and central agency 14). Although two workstations 24 have been shown in FIG. 2 for ease of illustration, it should be understood that laboratory 12a may include any number of workstations that are required for the provision of laboratory testing services.

Workstations 24 and LIS 22 preferably operate in a client-server environment, wherein each of workstations 24 operates as the "client" and LIS 22 operates as the "server." Workstations 24 communicate with LIS 22 via a communication network 30, such as an Ethernet network, a token ring network, or any other type of local area network or wide area network. Of course, other types of communication networks could also be used.

Referring still to FIG. 2, processor 26 of LIS 22 is operable to maintain in storage device 28 a database 32 that identifies various sets of relational data, including laboratory tests/test results, laboratory tests/internal laboratory statistical data, laboratory tests/group statistical summary data, and laboratory tests/control rules. Each set of relational data is preferably maintained in a separate table within database 32, although other database configurations could also be used. Of course, it should be understood that LIS 22 may include any relational database software that is suitable for maintaining the various sets of relational data in storage device 28.

A first set of relational data 34 maintained within database 32 comprises a plurality of laboratory tests 34a and the test results 34b corresponding to each of the laboratory tests 34a. The test results 34b for each of the laboratory tests 34a consist of a collection of test results that have been obtained from laboratory instruments 20 during the internal testing of quality control specimens within laboratory 12a. The first set of relational data will hereinafter be referred to as the "test results table 34."

A second set of relational data 36 maintained within database 32 comprises the plurality of laboratory tests 36a and the internal laboratory statistical data 36b corresponding to each of the laboratory tests 36a. The internal laboratory statistical data 36b consists of the statistical data (e.g., mean, median, standard deviation, coefficient of variation, standard deviation index, coefficient of variation index) derived from the test results 34b stored within test results table 34. As such, the internal laboratory statistical data 36a is based solely on the test results originating from laboratory 12a. The second set of relational data will hereinafter referred to as the "internal statistics table 36."

A third set of relational data 38 maintained within database 32 comprises the plurality of laboratory tests 38a and the group statistical summary data 38b corresponding to each of the laboratory tests 38a. As will be described in greater detail hereinbelow, the group statistical summary data 38b consists of the statistical data (e.g., mean, median, standard deviation, coefficient of variation, standard deviation index, coefficient of variation index) generated by central agency 14 for each of the laboratory tests. As such, the group statistical summary data 38b is based on the test results collected from all of the participating laboratories of system 10. The third set of relational data will hereinafter be referred to as the "group statistics table 38."

A fourth set of relational data 40 maintained within database 32 comprises the plurality of laboratory tests 40a and the control rules 40b corresponding to each of the laboratory tests 40a. Each of the control rules 40b consists of a formula that yields a lower limit value and an upper limit value, which together define a range of acceptable values (also known as a control range) for each of the laboratory tests. When performing a specified test on a quality control specimen, the test system is deemed to be in control when the test result falls within the control range and out of control when the control range is exceeded. The fourth set of relational data will hereinafter be referred to as the "control rules table 40."

In accordance with the present invention, the control rules 40b stored within control rules table 40 may be expressed in a variety of different ways. Some of the control rules may be expressed solely as a function of the group statistical summary data (e.g., group mean, group median, group standard deviation, group coefficient of variation, group standard deviation index, group coefficient of variation index) generated by central agency 14. For example, for some laboratory tests, the control rule may be expressed as a target plus or minus an absolute concentration (e.g., group mean±1 mg/dL). For other laboratory tests, the control rule may be expressed as a target plus or minus a percentage (e.g., group median±10%). For yet other laboratory tests, the control rule may be expressed as a target plus or minus the distribution of a survey group (e.g., group mean±3 group standard deviations). Thus, it can be seen that regardless of the type of control rule, the calculated control range is based solely on the group statistical summary data.

Other control rules may be expressed as a function of both the group statistical summary data (e.g., group mean, group median, group standard deviation, group coefficient of variation, group standard deviation index, group coefficient of variation index) generated by central agency 14 and the internal laboratory statistical data (e.g., internal mean, internal median, internal standard deviation, internal coefficient of variation, internal standard deviation index, internal coefficient of variation index) for laboratory 12a. For example, for some laboratory tests, the control rule may be expressed as a target plus or minus the distribution of a survey group (e.g., group mean±2 internal standard deviations). For other laboratory tests, the control rule may be expressed as a combination of two different control rules that must both be met for the test system to be deemed in control (e.g., internal mean±3 internal standard deviations, and, group mean±1.5 group standard deviations). For yet other laboratory tests, the control rule may be expressed relative to the standard deviation index (e.g., ((internal mean−group mean)/group standard deviation)>2) or the coefficient of variation index (e.g., (internal coefficient of variation/group coefficient of variation) >1.5). Thus, it can be seen that in either case, the calculated control range is based in part on the group statistical summary data and in part on the internal laboratory statistical data.

While various types of control rules have been described hereinabove, it should be understood to one skilled in the art that other types of control rules that may be expressed as a function of the group statistical summary data generated by central agency 14 and/or the internal laboratory statistical data for laboratory 12a could also be used.

Referring still to FIG. 2, processor 26 of LIS 22 is also operable to initiate the performance of various laboratory tests on laboratory instruments 20, preferably in response to commands entered by laboratory workers via workstations 24. Prior to performing a specified laboratory test on actual patient specimens, it is common practice to test at least one quality control specimen to verify that the test result falls within the control range for the specified laboratory test. To do so, the quality control specimen is tested on one of laboratory instruments 20 (i.e., the laboratory instrument to be used for testing the actual patient specimens), and the test result generated for that quality control specimen is transmitted from the laboratory instrument to processor 26. It should be understood that this process is repeated for each of the various quality control specimens that are tested on laboratory instruments 20.

Upon receipt of the new test results from laboratory instruments 20, processor 26 is operable to transfer the new test results to test results table 34 for storage in relation to the appropriate laboratory tests. Processor 26 is also operable to re-compute the internal laboratory statistical data for the laboratory tests from the collection of test results stored within test results table 34 (which now includes the new test results). Processor 26 is then operable to transfer the updated internal laboratory statistical data to internal statistics table 36 for storage in relation to the appropriate laboratory tests.

Processor 26 is further operable to evaluate the new test results received from laboratory instruments 20 to determine whether laboratory instruments 20 are "in control" or "out of control." To do so, processor 26 is operable to calculate the control ranges for the laboratory tests run on laboratory instruments 20. For example, for those laboratory tests having a control rule that is expressed solely as a function of the group statistical summary data, processor 26 is operable to calculate the control range by applying the group statistical summary data stored within group statistics table 38 to the control rule stored within control rules table 40. Alternatively, for those laboratory tests having a control rule that is expressed as a function of both the group statistical summary data and the internal laboratory statistical data, processor 26 is operable to calculate the control range by applying the group statistical summary data stored within group statistics table 38 and the internal laboratory statistical data stored within internal statistics table 36 to the control rule stored within control rules table 40. Processor 26 is then operable to compare the new test results to the calculated control ranges to determine whether the new test results fall within the calculated control ranges (whereby laboratory instruments 20 are deemed to be "in control") or whether one or more of the new test results exceed the control ranges (whereby one or more laboratory instruments 20 are deemed to be "out of control"). Preferably, processor 26 is operable to display the new test results, calculated control ranges and control status on workstations 24 so that a laboratory worker may manually review the data to determine whether a re-calibration of one or more laboratory instruments 20 is required.

Referring still to FIG. 2, processor 26 of LIS 22 is also operable to transmit the new test results received from laboratory instruments 20 over communication link 16*a* to central agency 14. Preferably, the new test results are transmitted to central agency 14 in response to a synchronization command entered by a laboratory worker via one of workstations 24. Alternatively, the new test results may be transmitted to central agency 14 at a specified date and time (e.g., every 8 hours of operation), or, the new test results may be transmitted to central agency 14 automatically as they become available. As will be described in greater detail with reference to FIG. 5, central agency 14 then updates the group statistical summary data with the new test results received from laboratory 12*a*, and automatically transmits the updated group statistical summary data back over communication link 16*a* to processor 26.

Upon receipt of the updated statistical summary data from central agency 14, processor 26 is operable to evaluate the updated group statistical summary data for correspondence with the current group statistical summary data stored in group statistics table 38. Preferably, the values of the updated group statistical summary data are compared with the values of the current group statistical summary data to determine whether there is a variance of more than a specified percentage (e.g. 10%). If there is such a variance, processor 26 is operable to flag the updated group statistical summary data for display on workstations 24 so that a laboratory worker may manually review the data for possible adjustment. If there is not such a variance, processor 26 is then operable to transfer the updated group statistical data to group statistics table 38 for storage in relation to the appropriate laboratory tests.

Figure 3:
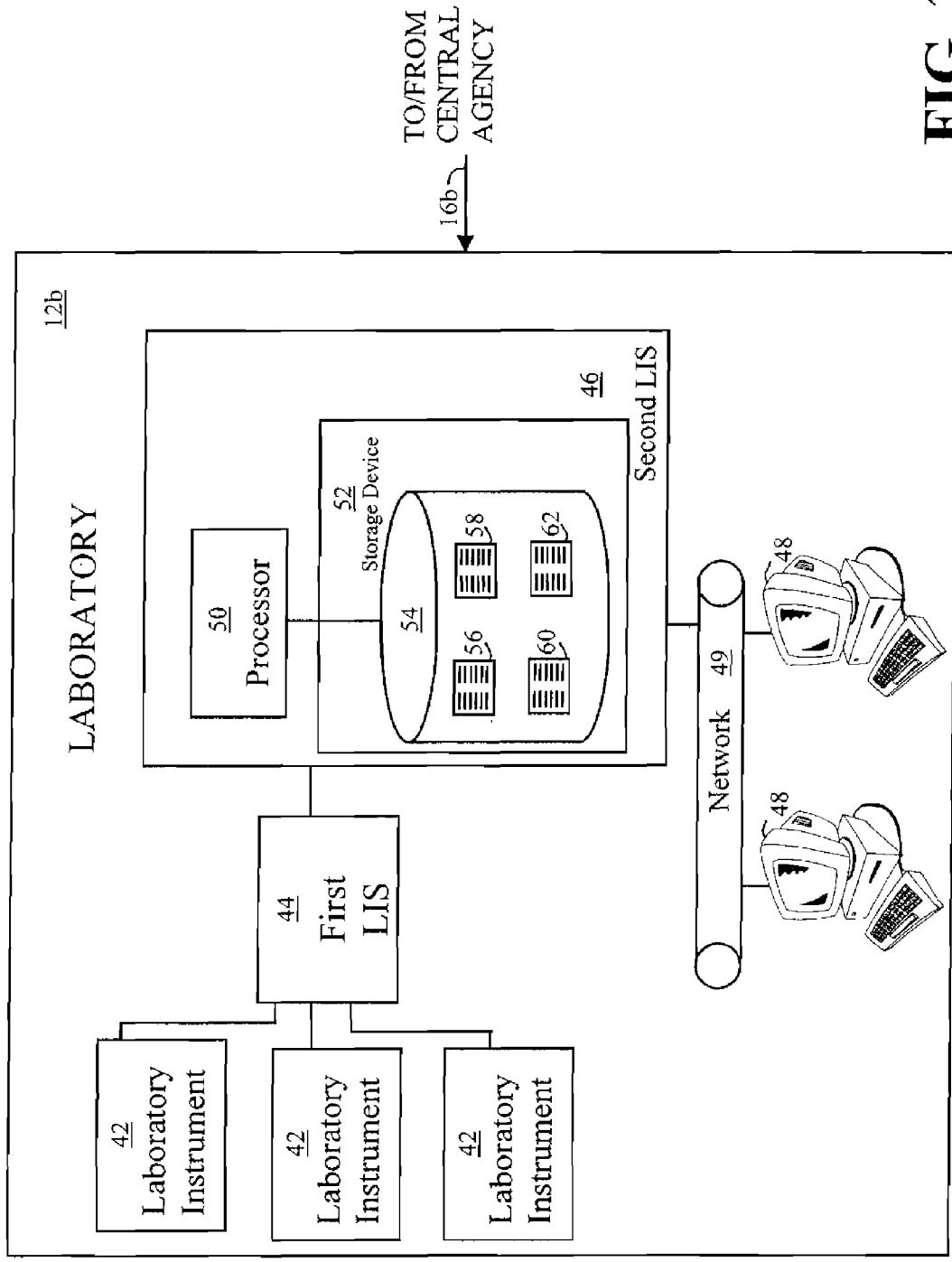
FIG. 3 is a block diagram of a second exemplary embodiment of one of the laboratories of FIG. 1.

Referring now to FIG. 3, a second exemplary embodiment of a system configuration for participating laboratories 12*a*-12*h* is shown with reference to laboratory 12*b*. Laboratory 12*h* includes one or more laboratory instruments 42 connected to a first laboratory information system (first LIS) 44, which is in turn connected to a second laboratory information system (second LIS) 46. Preferably, first LIS 44 and second LIS 46 are both connected to one or more workstations 48 via a communication network 49 for operation in a client-server environment. While laboratory instruments 42, first LIS 44, second LIS 46 and workstations 48 are shown as being co-located together within the same laboratory, it should be understood that one or more of these system elements could be located at a remote location (with suitable connections to the other system elements).

It can be seen that most of the system elements of laboratory 12*b* are the same as those of laboratory 12*a*. For example, laboratory instruments 42 are the same as laboratory instruments 20, and workstations 48 are the same as workstations 24. However, as will now be described, first LIS 44 and second LIS 46 are utilized in place of LIS 22 (which, as described hereinabove, is specifically configured to perform all of the various processes of the present invention).

First LIS 44 comprises a conventional computing system that is used to initiate the performance of various laboratory tests on laboratory instruments 42 and receive the test results therefrom. It should be understood that because first LIS 44 is a conventional system, it is not capable of utilizing the group statistical summary data generated by central agency 14 in connection with the internal testing of quality control specimens.

Second LIS 46 comprises a computing system that includes a processor 50 and a storage device 52. Examples of well-known computing systems that may be used for second LIS 46 include server computers, multiprocessor computers and mainframe computers, although other computing systems could also be used. Processor 50 is operable to execute computer-readable instructions stored on a computer-readable medium to thereby perform the additional processes of the present invention that are not performed by first LIS 44. The computer-readable instructions may be coded using the Delphi programming language, although other programming languages could also be used, such as C, C++, Visual Basic, Java, Smalltalk, Eiffle, PERL and FORTRAN. The computer-readable medium may include any type of computer memory, such as floppy disks, conventional hard disks, CD-ROMS, Flash ROMS, nonvolatile ROM and RAM.

In accordance with the present invention, processor 50 of second LIS 46 is operable to maintain in storage device 52 a database 54 that includes a test results table 56, an internal statistics table 58, a group statistics table 60 and a control rules table 62 (which are the same as the tables described hereinabove with reference to laboratory 12*a*). Processor 50 is also operable to import test results from first LIS 44 into second LIS 46 and transfer the imported test results to test results table 56 for storage in relation to the appropriate laboratory tests. Alternatively, the test results may be imported directly from laboratory instruments 42 into second LIS 46, or, manually entered into second LIS 46.

Processor 50 is also operable to re-compute the internal laboratory statistical data for the laboratory tests from the collection of test results stored within test results table 56, which now includes the imported test results. Processor 50 is then operable to transfer the updated internal laboratory statistical data to internal statistics table 58 for storage in relation to the appropriate laboratory tests.

Processor 50 is further operable to evaluate the imported test results to determine whether laboratory instruments 42 are "in control" or "out of control." To do so, processor 50 is operable to calculate the control ranges for the laboratory tests corresponding to the imported test results. Processor 26 is then operable to compare the imported test results to the calculated control ranges to determine whether the imported test results fall within the calculated control ranges (whereby laboratory instruments 42 are deemed to be "in control") or whether one or more of the imported test results exceed the control ranges (whereby one or more of laboratory instruments 42 are deemed to be "out of control"). Preferably, processor 50 is operable to display the imported test results, calculated control ranges and control status on workstations 48 so that a laboratory worker may manually review the data to determine whether a re-calibration of one or more laboratory instruments 42 is required.

Referring still to FIG. 3, processor 50 of second LIS 46 is also operable to transmit the imported test results over communication link 16b to central agency 14. Preferably, the imported test results are transmitted to central agency 14 in response to a synchronization command entered by a laboratory worker via one of workstations 48. Alternatively, the imported test results may be transmitted to central agency 14 at a specified date and time, or, the imported test results may be transmitted to central agency 14 automatically as they become available. As will be described in greater detail with reference to FIG. 5, central agency 14 then updates the group statistical summary data with the imported test results received from laboratory 12b, and automatically transmits the updated group statistical summary data back over communication link 16b to processor 50.

Upon receipt of the updated statistical summary data from central agency 14, processor 50 is operable to evaluate the updated group statistical summary data for correspondence with the current group statistical summary data stored in group statistics table 60. Preferably, the values of the updated group statistical summary data are compared with the values of the current group statistical summary data to determine whether there is a variance of more than a specified percentage. If there is such a variance, processor 50 is operable to flag the updated group statistical summary data for display on workstations 48 so that a laboratory worker may manually review the data for possible adjustment. If there is not such a variance, processor 50 is then operable to transfer the updated group statistical data to group statistics table 60 for storage in relation to the appropriate laboratory tests.

Figure 4:
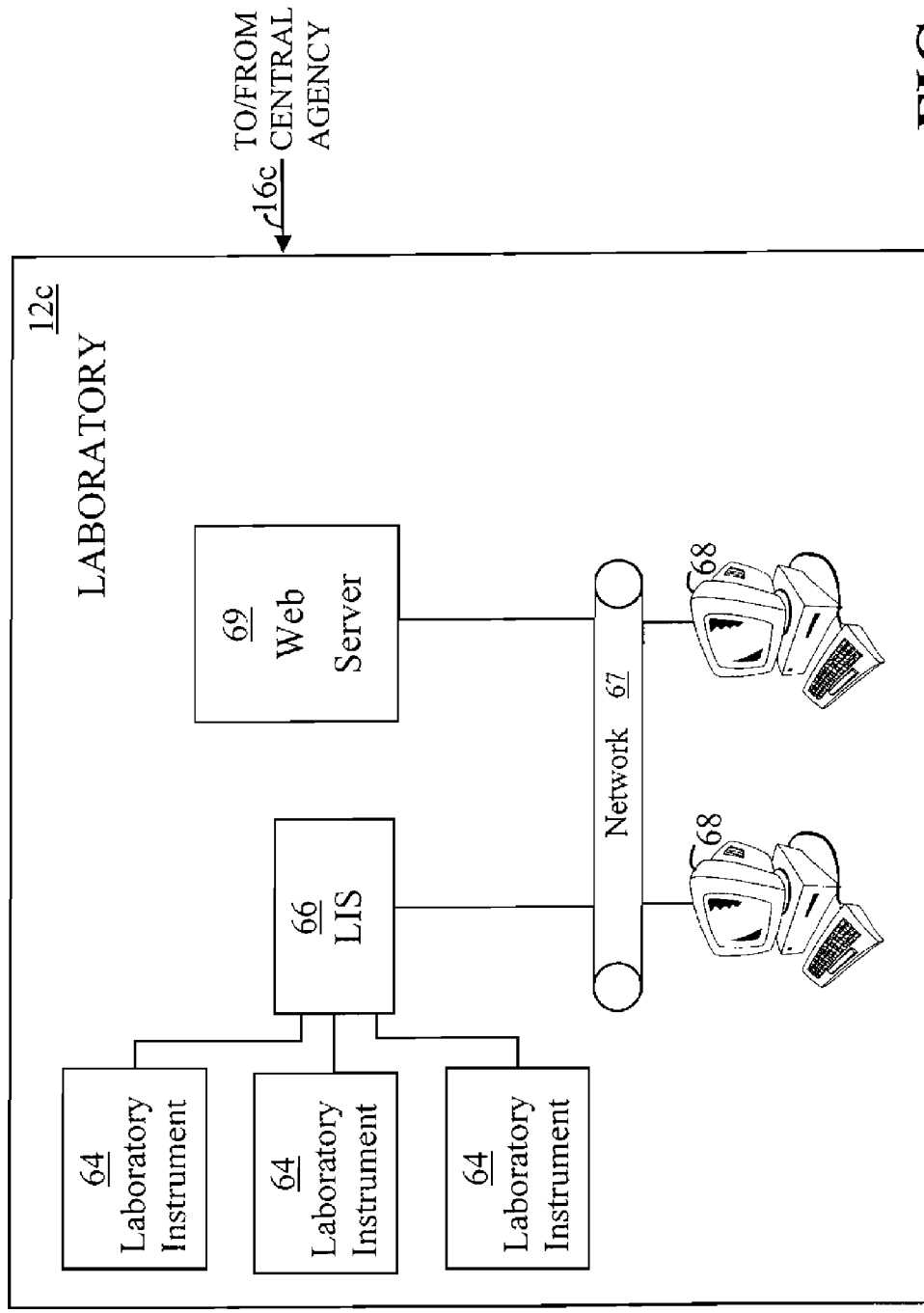
FIG. 4 is a block diagram of a third exemplary embodiment of one of the laboratories of FIG. 1.

Referring now to FIG. 4, a third exemplary embodiment of a system configuration for participating laboratories 12a-12h is shown with reference to laboratory 12c. Laboratory 12c includes one or more laboratory instruments 64 connected to a laboratory information system (LIS) 66, which is in turn connected to one or more workstations 68 via a communication network 67 for operation in a client-server environment. While laboratory instruments 64, LIS 66 and workstations 68 are shown as being co-located together within the same laboratory, it should be understood that one or more of these system elements could be located at a remote location (with suitable connections to the other system elements).

It can be seen that many of the system elements of laboratory 12c are the same as those of laboratory 12b. For example, laboratory instruments 64 are the same as laboratory instruments 42, workstations 68 are the same as workstations 48, and LIS 66 is the same as first LIS 44 (i.e., a conventional computing system that is used to initiate the performance of various laboratory tests on laboratory instruments 64 and receive the test results therefrom). However, laboratory 12c does not include a system element that corresponds to second LIS 46. Rather, the processes performed by second LIS 46 are performed by central agency 14 (which will be described in greater detail hereinbelow with reference to FIG. 5).

In order for central agency 14 to perform such processes, it must receive the test results from laboratory 12c. Accordingly, in one embodiment, a Web server 69 is provided that allows a laboratory worker to transfer the test results via e-mail over communication link 16c to central agency 14. Of course, other file exchange protocols could also be used, such as HTTP or FTP. Alternatively, in another embodiment, Web server 69 is provided to allow a laboratory worker to manually enter the test results via a manual input screen provided on an Internet web site of central agency 14. However, this alternative is not practical for laboratories that process large amounts of test results.

Finally, it should be understood that laboratories 12a, 12b and 12c have been described and illustrated hereinabove to show the variety of system configurations that are possible for laboratories 12a-12h. One skilled in the art will understand that other system configurations for laboratories 12a-12h could also be implemented in accordance with the present invention.

As will now be described with reference to FIG. 5, an exemplary embodiment of a system configuration for central agency 14 is shown. Central agency 14 comprises a central computing system 70 that includes a central processor 72 and a central storage device 74. Examples of well-known computing systems that are suitable for use with the present invention include server computers, multiprocessor computers and mainframe computers, although other computing systems could also be used.

Central processor 72 is operable to execute computer-readable instructions stored on a computer-readable medium to thereby perform the various processes of the present invention, as will be described in greater detail hereinbelow. The computer-readable instructions may be coded using the Delphi programming language, although other programming languages could also be used, such as C, C++, Visual Basic, Java, Smalltalk, Eiffle, PERL and FORTRAN. The computer-readable medium may include any type of computer memory, such as floppy disks, conventional hard disks, CD-ROMS, Flash ROMS, nonvolatile ROM and RAM.

Figure 5:
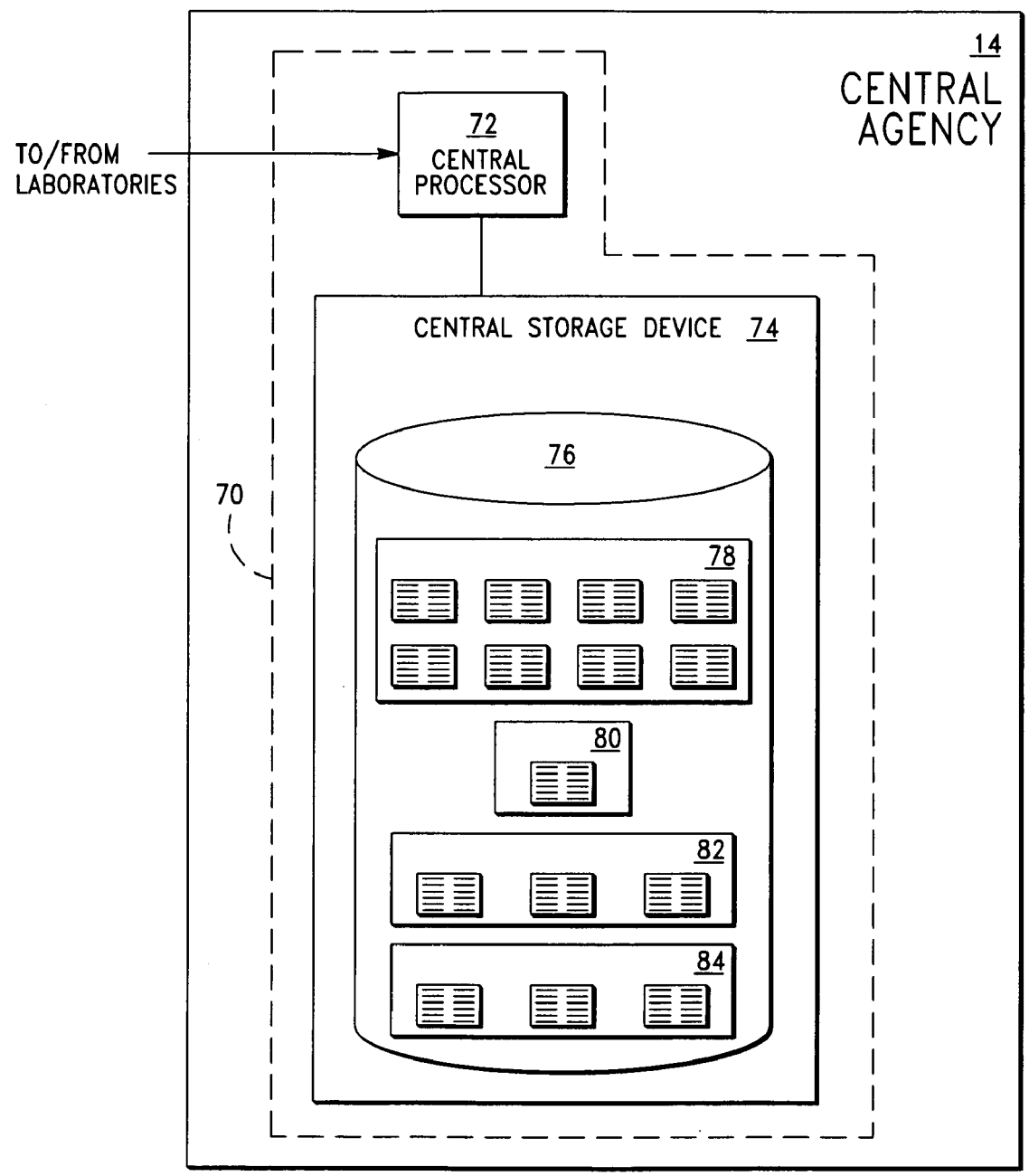
FIG. 5 is a block diagram of an exemplary embodiment of the central agency of FIG. 1.

Referring still to FIG. 5, central processor 72 is operable to maintain in central storage device 74 a central database 76 that identifies various groups and sets of relational data, as described hereinbelow. Each set of relational data is preferably maintained in a separate table within central database 76, although other database configurations could also be used. Of course, it should be understood that central computing system 70 may include any relational database software that is suitable for maintaining the various sets of relational data in central storage device 74.

A first group of relational data 78 maintained within central database 76 comprises a plurality of individual sets of relational data (one for each of the participating laboratories of system 10). Each set of relational data comprises a plurality of laboratory tests and the collection of test results corresponding to each of the laboratory tests for that particular laboratory. This group of relational data will hereinafter be referred to as the "group of test results tables 78."

Another set of relational data 80 maintained within central database 76 comprises the plurality of laboratory tests and the group statistical summary data corresponding to each of the laboratory tests (which is derived from testing carried out by specified groups of laboratory instruments within the participating laboratories of system 10). This set of relational data will hereinafter be referred to as the "group statistics table 80."

Another group of relational data 82 maintained within central database 76 comprises a plurality of individual sets of relational data (one for each of the participating laboratories of system 10 that have the system configuration of laboratory 12*c*). Each set of relational data comprises the plurality of laboratory tests and the internal laboratory statistical data corresponding to each of the laboratory tests for that particular laboratory. This group of relational data will hereinafter referred to as the "group of internal statistics tables 82."

Yet another group of relational data 84 maintained within central database 76 comprises a plurality of individual sets of relational data (one for each of the participating laboratories of system 10 that have the system configuration of laboratory 12*c*). Each set of relational data comprises the plurality of laboratory tests and the control rules corresponding to each of the laboratory tests for that particular laboratory. This group of relational data will hereinafter be referred to as the "group of control rules tables 84."

Referring still to FIG. 5, central processor 72 is also operable to periodically receive tests results from the various participating laboratories of system 10. For a participating laboratory that has the system configuration of laboratory 12*a* (see FIG. 2) or laboratory 12*b* (see FIG. 3), the test results are transmitted from the participating laboratory over a communication link for receipt by central processor 72. Upon receipt of the test results, central processor 72 is operable to transfer the test results to the appropriate table within the group of test results tables 78 (i.e., the table assigned to that particular laboratory) for storage in relation to the appropriate laboratory tests. Central processor 26 is also operable to re-compute the group statistical summary data for the laboratory tests from the collection of test results stored within the group of test results tables 78, which now includes the new test results. Central processor 72 is then operable to transfer the updated group statistical summary data to group statistics table 80 for storage in relation to the appropriate laboratory tests. In addition, central processor 72 is operable to transmit the updated group statistical summary data back over the communication link to the participating laboratory.

For a participating laboratory that has the system configuration of laboratory 12*c* (see FIG. 4), the test results are either sent via e-mail over a communication link for receipt by central processor 72 or are manually entered via a manual input screen provided on the Internet web site of central agency 14 for receipt by central processor 72. Regardless of the manner in which the test results are received, central processor 72 is operable to transfer the test results to the appropriate table within the group of test results tables 78 (i.e., the table assigned to that particular laboratory) for storage in relation to the appropriate laboratory tests.

Central processor 72 is also operable to re-compute the internal laboratory statistical data for the laboratory tests from the collection of test results stored within the appropriate table of the group of test results tables 78 (i.e., the table assigned to that particular laboratory), which now includes the new test results. Central processor 72 is then operable to transfer the updated internal laboratory statistical data to the appropriate table of the group of internal statistics tables 82 (i.e., the table assigned to that particular laboratory) for storage in relation to the appropriate laboratory tests.

In addition, central processor 72 is operable to re-compute the group statistical summary data for the laboratory tests from the collection of test results stored within the group of test results tables 78, which now includes the new test results. Central processor 72 is then operable to transfer the updated group statistical summary data to group statistics table 80 for storage in relation to the appropriate laboratory tests.

Central processor 72 is further operable to evaluate the new test results to determine whether the laboratory instruments of the participating laboratory are "in control" or "out of control." To do so, central processor 72 is operable to calculate the control ranges for the laboratory tests corresponding to the new test results. Central processor 72 is then operable to compare the new test results with the calculated control ranges to determine whether the new test results fall within the calculated control ranges (whereby the laboratory instruments are deemed to be "in control") or whether one or more of the new test results exceed the control ranges (whereby one or more of the laboratory instruments are deemed to be "out of control").

Finally, for a participating laboratory that sends its test results to central agency 14 via e-mail, central processor 72 is preferably operable to send an e-mail back to the laboratory summarizing the new test results, calculated control ranges and control status so that a laboratory worker may review the data to determine whether a re-calibration of one or more of the laboratory instruments is required. Alternatively, for a participating laboratory that manually enters its test results on the Internet web site of central agency 14, central processor 72 is preferably operable to post the new test results, calculated control ranges and control status to the Internet web site so that a laboratory worker may access the Internet web site (preferably via appropriate authentication procedures, such as a user ID and password) and review the data to determine whether a re-calibration of one or more of the laboratory instruments is required.

Figure 6A:
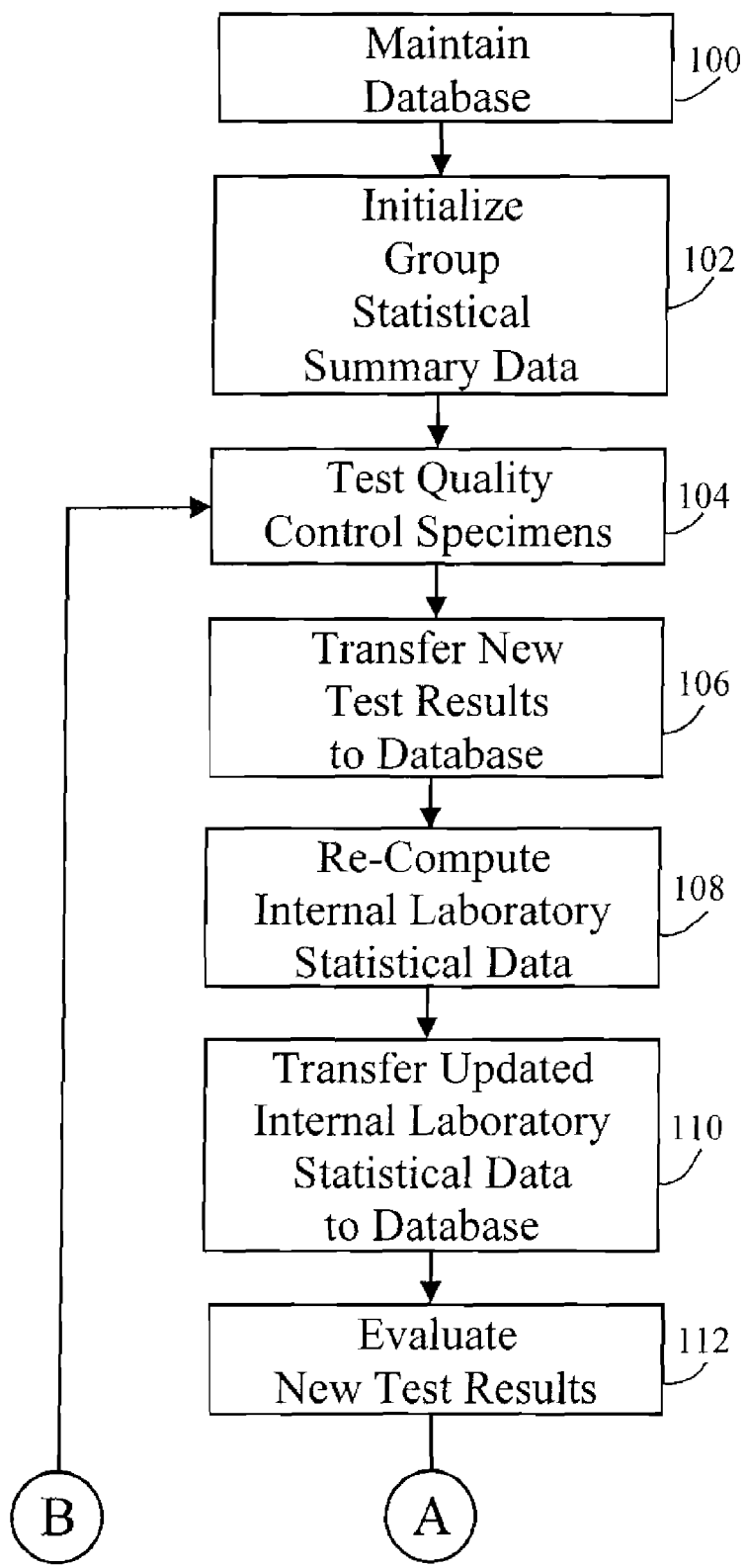
FIGS. 6A and 6B are flow charts of a method for integrating the internal and external quality control programs of a laboratory, in accordance with the present invention.
Figure 6B:
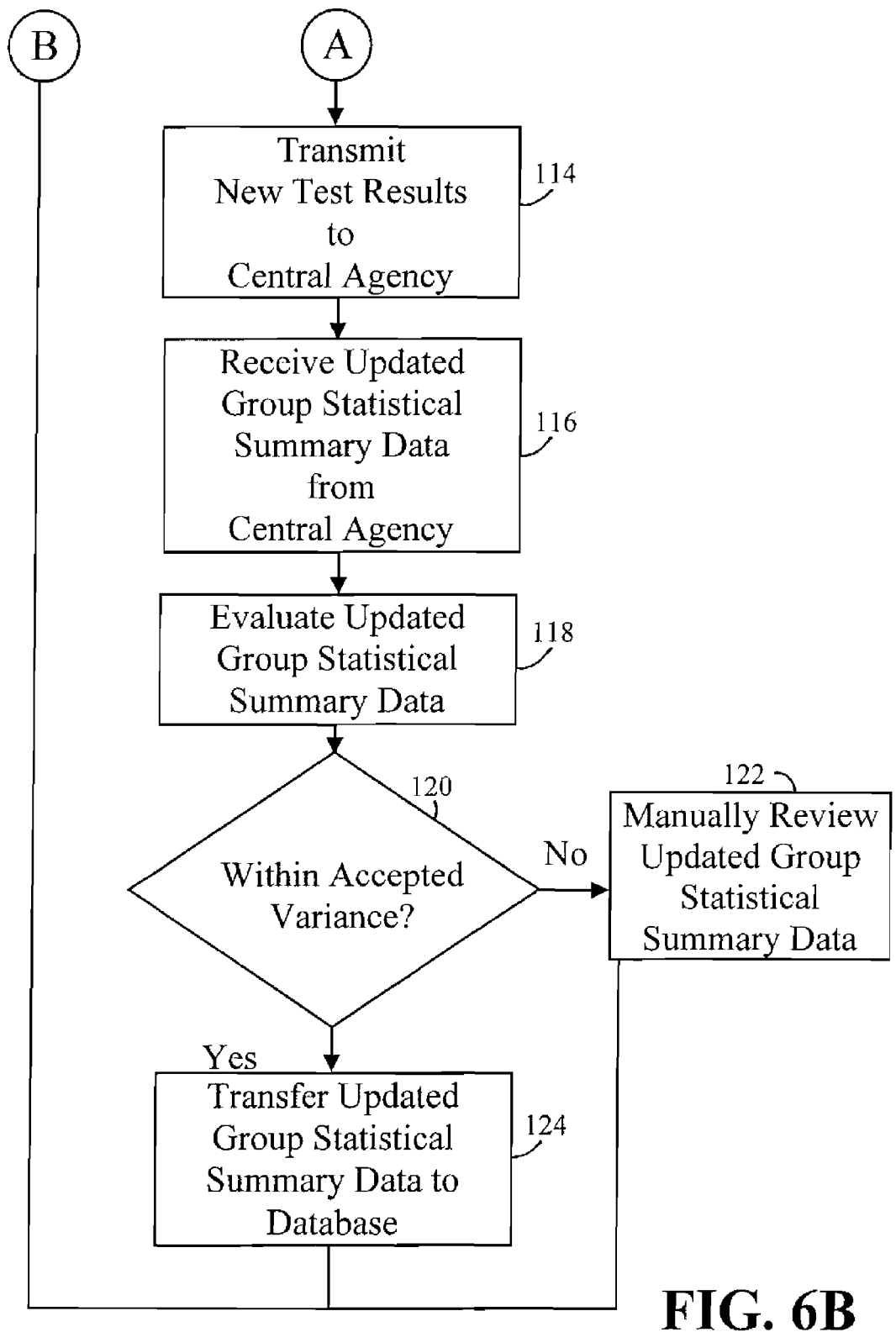

Turning now to FIGS. 6A and 6B, a flow diagram of a computerized method in accordance with the present invention is provided with reference to blocks 100-124. At block 100, a database is maintained that identifies various sets of relational data, including laboratory tests/test results, laboratory tests/internal laboratory statistical data, laboratory tests/ group statistical summary data, and laboratory tests/control rules. Then, at block 102, the set of relational data containing the laboratory tests/group statistical summary data is initialized to contain the updated group statistical data received from a central agency.

At block 104, various laboratory tests are performed on various quality control specimens using one or more laboratory instruments. Then, at block 106, the new test results generated by the laboratory instruments are transferred to the set of relational data containing the laboratory tests/test results for storage in relation to the appropriate laboratory tests.

Next, at block 108, the internal laboratory statistical data is re-computed for each of the laboratory tests using the test results stored within the set of relational data containing the laboratory tests/test results (which now includes the new test results). Then, at block 110, the updated internal laboratory statistical data is transferred to the set of relational data containing the laboratory tests/internal laboratory statistical data for storage in relation to the appropriate laboratory tests.

At block 112, the new test results are evaluated to determine whether the laboratory instruments are "in control" or "out of control." To do so, the control ranges for the laboratory tests are calculated and compared with the new test results. If the new test results fall within the calculated control ranges, then the laboratory instruments are deemed to be "in control" and the method proceeds directly to block 114. However, if one or more of the new test results exceeds the calculated control ranges, then one or more of the laboratory instruments are deemed to be "out of control." In such a case, the new test results, calculated control ranges and control status are flagged for manual review by a laboratory worker to determine whether re-calibration of one or more of the laboratory instruments is required.

At block 114, the new test results are transmitted to the central agency. The new test results may be transmitted to the central agency in response to a synchronization command entered by a laboratory worker, at a specified date and time, automatically as new test results become available, via e-mail, or by manual entry. The central agency 14 then updates the group statistical summary data with the new test results. Then, at block 116, the updated group statistical summary data is received from the central agency.

At block 118, the updated group statistical summary data is evaluated for correspondence with the current group statistical summary data stored in the set of relational data containing the laboratory tests/group statistical summary data. Specifically, the values of the updated group statistical summary data are compared with the values of the current group statistical summary data to determine the variance therebetween. At block 120, it is determined whether the variance is acceptable. If the variance is not acceptable, at block 122 the updated group statistical summary data is flagged for manual review by a laboratory worker for possible adjustment. On the other hand, if the variance is acceptable, at block 124 the updated group statistical summary data is transferred to the set of relational data containing the laboratory tests/group statistical summary data for storage in relation to the appropriate laboratory tests. Finally, the method returns to step 104 to repeat the processes of blocks 106-124 for another group of various laboratory tests performed on various quality control specimens using one or more laboratory instruments.

It should be apparent to one skilled in the art that the system and method of the present invention described and illustrated hereinabove provide several advantages over traditional practices that do not integrate the internal and external quality control programs of a laboratory. For example, over time, the "tweaking" of small adjustments into the group statistical summary data generated by a central agency will reduce the variation in test results experienced among participating laboratories of an external quality control program.

Also, because participating laboratories are continually updating the group statistical summary data used to calculate the control ranges for internal laboratory testing, certain test results may be accepted that would otherwise be considered erroneous under a traditional analysis (which does not utilize the group statistical summary data). Conversely, certain test results may be considered erroneous that would otherwise be accepted under a traditional analysis.

In addition, because a majority of the federally mandated laboratory performance standards (e.g., outlined in CLIA Regulations 493 and 909-959) are specified as a function of the group statistical summary data, the use of the group statistical summary data to calculate the control ranges for internal laboratory testing allows laboratories to base their internal quality control practices on the same principles used by federal regulatory agencies to evaluate laboratory quality.

While the present invention has been described and illustrated hereinabove with reference to several exemplary embodiments, it should be understood that various modifications could be made to these embodiments without departing from the scope of the invention. Therefore, the invention is not to be limited to the specific systems and methods described and illustrated hereinabove, except insofar as such limitations are included in the following claims.

What is claimed and desired to be secured by Letters Patent is as follows:

1. A system for integrating the internal and external quality control programs of a laboratory utilizing control rules for specified laboratory tests, comprising:
   at least one storage device located at a laboratory;
   at least one processor located at the laboratory that is operable to:
      maintain in the storage device at least one database identifying a plurality of laboratory tests and corresponding group statistical summary data, the database also identifying the plurality of laboratory tests and corresponding control rules expressed as a function of the group statistical summary data;
      calculate a control range for a specified one of the laboratory tests by applying the group statistical summary data for the specified laboratory test to the control rule for the specified laboratory test whereby the calculated control range defines an acceptable range of test result values for the specified laboratory test;
      receive a test result from a laboratory instrument at the laboratory for the specified one of the laboratory tests;
      determine whether the test result falls within the calculated control range for the specified laboratory test;
      receive updated group statistical summary data from a central agency and determine the variance between the updated group statistical summary data and the group statistical summary data; and
      display the updated group statistical summary data for user review if the variance between the updated group statistical summary data and the group statistical summary data exceeds a specified percentage.

2. The system of claim 1, wherein the processor is further operable to display the test result and calculated control range so that a user at the laboratory can review the test result and calculated control range to determine whether re-calibration of the laboratory instrument is required.

3. The system of claim 1, wherein the group statistical summary data is selected from the following group: a mean, a median, a standard deviation, a coefficient of variation, a standard deviation index, a coefficient of variation index, and combinations thereof.

4. The system of claim 1, wherein the database also identifies the plurality of laboratory tests and corresponding internal laboratory statistical data, and wherein the processor is operable to calculate the control range for the specified one of the laboratory tests by applying both the group statistical summary data for the specified laboratory test and the internal laboratory statistical data for the specified laboratory test to the control rule for the specified laboratory test.

5. The system of claim 1, wherein the processor is further operable to receive updated group statistical summary data from a central agency and transfer the updated group statistical summary data to the database whereby the updated group statistical summary data becomes the group statistical summary data.

6. The system of claim 5, wherein the updated group statistical summary data received from the central agency is derived from testing carried out by a specified group of laboratory instruments.

7. The system of claim 5, wherein the processor receives the updated group statistical summary data from the central agency over the Internet.

8. The system of claim 5, wherein the processor is operable to transfer the updated group statistical summary data received from the central agency to the database prior to calculating the control range for the specified one of the laboratory tests.

9. The system of claim 5, wherein the processor receives the updated group statistical summary data from the central agency at a specified date and time.

10. The system of claim 1, wherein the processor is further operable to receive updated group statistical summary data from a central agency in response to a synchronization command.

11. The system of claim 1, wherein the processor is further operable to transmit the test result to a central agency.

12. The system of claim 1, further comprising:
at least one central storage device;
at least one central processor operable to:
maintain in the central storage device at least one central database identifying the plurality of laboratory tests and corresponding updated group statistical summary data; and
transmit the updated group statistical summary data to the processor.

13. The system of claim 12, wherein the central storage device and the central processor are located at a central agency.

14. The system of claim 12, wherein the central processor is further operable to receive a plurality of test results from a plurality of laboratory instruments for incorporation into the updated group statistical summary data.

15. A computerized method for integrating the internal and external quality control programs of a laboratory utilizing control rules for specified laboratory tests, comprising:
maintaining at least one database at a laboratory identifying a plurality of laboratory tests and corresponding group statistical summary data, the database also identifying the plurality of laboratory tests and corresponding control rules expressed as a function of the group statistical summary data;
calculating a control range at the laboratory for a specified one of the laboratory tests by applying the group statistical summary data for the specified laboratory test to the control rule for the specified laboratory test whereby the calculated control range defines an acceptable range of test result values for the specified laboratory test;
receiving a test result from a laboratory instrument at the laboratory for the specified one of the laboratory tests;
determining at the laboratory whether the test result falls within the calculated control range for the specified laboratory test;
receiving updated group statistical summary data from a central agency, and determining the variance between the updated group statistical summary data and the group statistical summary data; and
displaying the updated group statistical summary data for user review if the variance between the updated group statistical summary data and the group statistical summary data exceeds a specified percentage.

16. The computerized method of claim 15, wherein the group statistical summary data is selected from the following group: a mean, a median, a standard deviation, a coefficient of variation, a standard deviation index, a coefficient of variation index, and combinations thereof.

17. The computerized method of claim 15, wherein the database also identifies the plurality of laboratory tests and corresponding internal laboratory statistical data, and wherein the control range for the specified one of the laboratory tests is calculated by applying both the group statistical summary data for the specified laboratory test and the internal laboratory statistical data for the specified laboratory test to the control rule for the specified laboratory test.

18. The computerized method of claim 15, further comprising receiving updated group statistical summary data from a central agency and transferring the updated group statistical summary data to the database whereby the updated group statistical summary data becomes the group statistical summary data.

19. The computerized method of claim 18, wherein the updated group statistical summary data received from the central agency is derived from testing carried out by a specified group of laboratory instruments.

20. The computerized method of claim 18, wherein the updated group statistical summary data received from the central agency is transferred to the database prior to calculating the control range for the specified one of the laboratory tests.

21. The computerized method of claim 18, wherein the updated group statistical summary data is received from the central agency at a specified date and time.

22. The computerized method of claim 15, further comprising displaying the test result and calculated control range so that a user at the laboratory can review the test result and calculated control range to determine whether re-calibration of the laboratory instrument is required.

23. The computerized method of claim 15, further comprising transmitting the test result to a central agency.

24. The computerized method of claim 15, further comprising receiving updated group statistical summary data from a central agency in response to a synchronization command.

25. A computer-readable medium having computer-executable instructions for performing a method of integrating the internal and external quality control programs of a laboratory utilizing control rules for specified laboratory tests, the method comprising:
maintaining at least one database at a laboratory identifying a plurality of laboratory tests and corresponding group statistical summary data, said database further identifying the plurality of laboratory tests and corresponding control rules expressed as a function of the group statistical summary data;
calculating a control range at the laboratory for a specified one of the laboratory tests by applying the group statistical summary data for the specified laboratory test to the corresponding control rule whereby the calculated control range defines an acceptable range of test result values for the specified laboratory test;
receiving a test result from a laboratory instrument at the laboratory for the specified one of the laboratory tests;
determining at the laboratory whether the test result falls within the calculated control range for the specified laboratory test;
receiving updated group statistical summary data from a central agency, and determining the variance between the updated group statistical summary data and the group statistical summary data; and
displaying the updated group statistical summary data for user review if the variance between the updated group statistical summary data and the group statistical summary data exceeds a specified percentage.

26. The computer-readable medium of claim 25, wherein the group statistical summary data is selected from the following group: a mean, a median, a standard deviation, a coefficient of variation, a standard deviation index, a coefficient of deviation index, and combinations thereof.

27. The computer-readable medium of claim 25, wherein the database also identifies the plurality of laboratory tests and the corresponding internal laboratory statistical data, and wherein the control range for the specified one of the laboratory tests is calculated by applying both the corresponding group statistical summary data and the corresponding internal laboratory statistical data to the corresponding control rule.

28. The computer-readable medium of claim 25, wherein the method further comprises receiving updated group statistical summary data from a central agency and transferring the updated group statistical summary data to the database whereby the updated group statistical summary data becomes the group statistical summary data.

29. The computer-readable medium of claim 28, wherein the updated group statistical summary data received from the central agency is derived from testing carried out by a specified group of laboratory instruments.

30. The computer-readable medium of claim 28, wherein the updated group statistical summary data received from the central agency is transferred to the database prior to calculating the control range for the specified one of the laboratory tests.

31. The computer-readable medium of claim 28, wherein the updated group statistical summary data is received from the central agency at a specified date and time.

32. The computer-readable medium of claim 25, wherein the method further comprises displaying the test result and calculated control range so that a user at the laboratory can review the test result and calculated control range to determine whether re-calibration of the laboratory instrument is required.

33. The computer-readable medium of claim 25, wherein the method further comprises transmitting the test result to a central agency.

34. The computer-readable medium of claim 25, wherein the method further comprises receiving updated group statistical summary data from a central agency in response to a synchronization command.

35. A system for integrating the internal and external quality control programs of a laboratory utilizing control rules for specified laboratory tests, comprising:
   means for maintaining at least one database at a laboratory identifying a plurality of laboratory tests and the corresponding group statistical summary data and for identifying the plurality of laboratory tests and corresponding control rules expressed as a function of the group statistical summary data;
   means for calculating a control range at the laboratory for a specified one of the laboratory tests by applying the group statistical summary data corresponding to the specified laboratory test to the corresponding control rule whereby the calculated control range defines an acceptable range of test result values for the specified laboratory test;
   means for receiving a test result from a laboratory instrument at the laboratory for the specified one of the laboratory tests;
   means for determining at the laboratory whether the test result falls within the calculated control range for the specified laboratory test;
   means for receiving updated group statistical summary data from a central agency, and determining the variance between the updated group statistical summary data and the group statistical summary data; and
   means for displaying the updated group statistical summary data for user review if the variance between the updated group statistical summary data and the group statistical summary data exceeds a specified percentage.

36. The system of claim 35, wherein the database means also identifies the plurality of laboratory tests and the corresponding internal laboratory statistical data, and wherein the calculating means calculates the control range for the specified one of the laboratory tests by applying both the corresponding group statistical summary data and the corresponding internal laboratory statistical data to the corresponding control rule.

37. The system of claim 35, further comprising:
   means for receiving updated group statistical summary data from a central agency; and
   means for transferring the updated group statistical summary data to the database means whereby the updated group statistical summary data becomes the group statistical summary data.

38. The system of claim 35, further comprising means for displaying the test result and calculated control range so that a user at the laboratory can review the test result and calculated control range to determine whether re-calibration of the laboratory instrument is required.

39. The system of claim 35, further comprising means for transmitting the test result to a central agency.

40. A computer-readable medium having computer-executable instructions for performing a method of integrating the internal and external quality control programs of a laboratory utilizing control rules for specified laboratory tests, the method comprising:
   maintaining at least one database at a laboratory identifying a plurality of laboratory tests and the corresponding group statistical summary data and the database also identifying the corresponding control rules;
   receiving updated group statistical summary data from a central agency;
   determining the variance between the updated group statistical summary data and the group statistical summary data;
   displaying the updated group statistical summary data for user review if the variance between the updated group statistical summary data and the group statistical summary data exceeds a specified percentage;
   transferring the updated group statistical summary data to the database whereby the updated group statistical summary data becomes the group statistical summary data;
   receiving a test result from a laboratory instrument at the laboratory for a specified one of the laboratory tests;
   calculating a control range at the laboratory for the specified laboratory test by applying the corresponding group statistical summary data to the corresponding control rule; and
   determining at the laboratory whether the test result falls within the calculated control range.

41. The computer-readable medium of claim 40, wherein the database also identifies the plurality of laboratory tests and the corresponding internal laboratory statistical data, and wherein the control range for the specified one of the laboratory tests is calculated by applying both the group statistical summary data for the test and the internal laboratory statistical data for the test to the corresponding control rule.

42. The computer-readable medium of claim 40, wherein the updated group statistical summary data received from the central agency is transferred to the database prior to calculating the control range for the specified one of the laboratory tests.

43. The computer-readable medium of claim 40, wherein the updated group statistical summary data is received from the central agency at a specified date and time.

44. The computer-readable medium of claim 40, wherein the method further comprises transmitting the test result to the central agency.

45. The computer-readable medium of claim 40, wherein the method further comprises displaying the test result and calculated control range so that a user at the laboratory can review the data to determine whether re-calibration of the laboratory instrument is required.

\* \* \* \* \*